United States Patent [19]

Kelly

[11] Patent Number: 4,500,438
[45] Date of Patent: Feb. 19, 1985

[54] MULTI-RING FLUORINATED CARBAMATES WITH TEXTILE SOIL REPELLENT ACTIVITY

[75] Inventor: Michael G. Kelly, Coventry, R.I.

[73] Assignee: American Hoechst Corporation, Somerville, N.J.

[21] Appl. No.: 507,407

[22] Filed: Jun. 24, 1983

[51] Int. Cl.³ .................... D06M 13/40; C07C 125/06
[52] U.S. Cl. .................................. 252/8.75; 252/8.8; 560/27; 427/394
[58] Field of Search ................... 252/8.75, 8.8; 560/27

[56] References Cited

U.S. PATENT DOCUMENTS

| | | | |
|---|---|---|---|
| 3,171,861 | 3/1965 | Ahlbrecht | 260/633 |
| 3,484,281 | 12/1969 | Guenthner et al. | 117/121 |
| 3,646,153 | 2/1972 | Oxenrider et al. | 260/78 S |
| 3,657,320 | 4/1972 | Anello et al. | 260/471 C |
| 4,435,294 | 3/1984 | Oxenrider et al. | 252/8.8 |

FOREIGN PATENT DOCUMENTS 46-348 1/1971 Japan.
54-133485 10/1979 Japan.

Primary Examiner—Maria Parrish Tungol
Attorney, Agent, or Firm—Hugh C. Crall

[57] ABSTRACT

Multi-ring fluorinated carbamates are disclosed which have excellent anti-soiling properties, durability and resistance to laundering. The compounds are represented by the formula

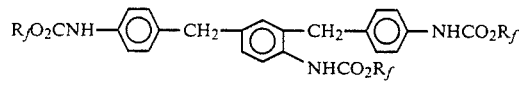

wherein $R_f$ is a fluorinated radical. Compositions containing at least 10% of such compounds are also disclosed, as well as polyester and nylon fibers having such compounds incorporated therein.

10 Claims, No Drawings

MULTI-RING FLUORINATED CARBAMATES WITH TEXTILE SOIL REPELLENT ACTIVITY

BACKGROUND OF THE INVENTION

This invention relates to fluorinated compositions which impart oil and water repellency to synthetic fibers, particularly polyester and nylon fibers, and thus function as anti-soil agents. In particular, this invention relates to fluorinated aromatic carbamates which are derived from fluorinated alcohols and multi-ring aromatic isocyanates.

DESCRIPTION OF THE PRIOR ART

Compounds containing fluorinated groups are broadly known for use as anti-soil agents for synthetic fibers. Fluorinated polyacrylates are disclosed in U.S. Pat. No. 3,171,861, U.S. Pat. No. 3,547,861 and U.S. Pat. No. 3,818,074. These compositions are generally not suitable for application to fibers prior to manufacture of textile fabric or prior to the dyeing of such fabric. In U.S. Pat. No. 3,171,861 it is indicated that the fluorinated alcohol starting materials can be reacted with isocyanates to form carbamates. However, the only carbamate prepared is one based on toluene diisocyanate (Example 10). In U.S. Pat. No. 3,646,153 a variety of fluorinated compositions are disclosed, including substituted ureas of the formula $$(R_fCNHCH_2CH_2)_2N-\overset{O}{\overset{\|}{C}}NH-R-NH\overset{O}{\overset{\|}{C}}-N(CH_2CH_2NH\overset{O}{\overset{\|}{C}}R_f)_2$$

wherein R is alkyl, alkylene, aryl, aralkyl or aralkylene (see col. 4, line 56et seq).

Fluorinated carbamates, derived from the reaction of perfluoroalkanols with isocyanates, are disclosed in U.S. Pat. No. 3,657,320. Typical of these is the compound having the formula

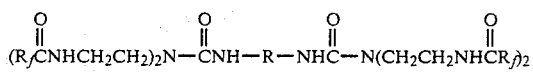

which is shown in Example 8 of said patent. Fluorinated carbamates are also disclosed in J54-133,485. Specifically, a water soluble dispersion of the compounds

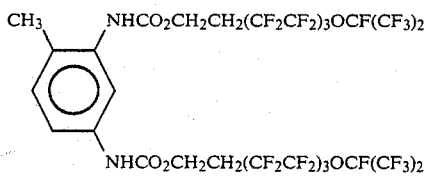

is shown in Example 9 of said application.

In U.S. Pat. No. 3,484,281 there is broadly disclosed a wide range of possible fluorinated carbamates. Typical of these are the compounds of the formula

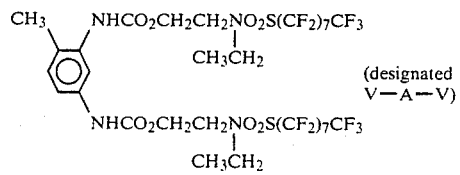
(designated V—A—V)

and

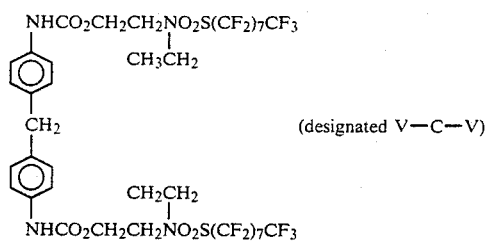
(designated V—C—V)

which are disclosed in Examples 3 and 4 (fifth compound in list) respectively. Also disclosed in a list of possible isocyanate starting materials is the compound

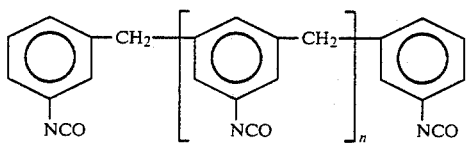

which is designated J in Table III. However, this isocyanate, as well as five others in the Table, are not mentioned again in the specification, nor are any fluorinated derivatives of them prepared or evaluated.

In Japanese Pat. No. J46-348 there is generally disclosed soil-repellent carbamates of the formula

[R$_f$]—X—CONH—[A]—NHCO—[Y]

wherein R$_f$ is a fluorinated hydrocarbon, X is preferably —O—, —S—, or —NR—, A is a diisocyanate residue (e.g. toluene diisocyanate) and Y is a stabilizing organic residue (e.g. phenoxy). A typical compound has the formula

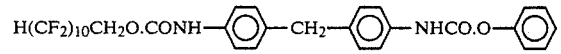

as shown in Example 1 of said patent. It appears that the compounds containing the stabilizing group Y are considered preferable to those having a free isocyanate group or where Y is —X—R$_f$.

SUMMARY OF THE INVENTION

Applicants have discovered a novel group of fluorinated aromatic carbamates which have excellent antisoiling properties, durability and resistance to laundering (wash-fastness) when incorporated in polyester and nylon fibers. The compounds of the present invention may be depicted by the formula (I)

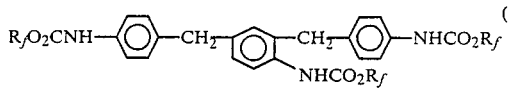
(I)

wherein $R_f$ is a fluorinated radical of the formula $-W(C_nF_{2n})Y$ wherein W has from 1 to 10 carbon atoms and is selected from alkylene and $W'-Z-(W'')_b$ where W' and W'' are alkylene, Z is O, S, NHCO, or $N(R)SO_2$ wherein R is H or lower alkyl, and b is 0 or 1, Y is hydrogen, fluoro, or perfluoroalkoxy of 1 to 6 carbon atoms, and n is 2 to 20. In the above formulation it is intended that the fluorinated radical $R_f$ may be straight, branched or cyclic in any of its alkylene or perfluoroalkylene chains, and lower alkyl means alkyl of 1 to 4 carbon atoms.

Also encompassed within the present invention are compositions containing at least 10% of the above-identified compound (I) in admixture with from 90 to 5% of a compound of the formula (II)

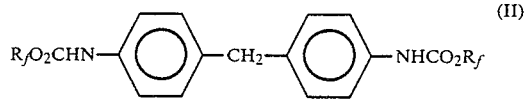
(II)

and optionally including from 0 to 30% of isomers and homologues of these two compounds.

The subject compounds have an excellent affinity for polyester and nylon fibers and may be incorporated with the raw or partially finished fiber by several methods. In one method the additive may be melt blended with the resin then extruded to form a fiber. In a second method the fiber may be treated with a solution, dispersion or emulsion of the additive in liquid medium, typically a solution in organic solvent or an aqueous emulsion. Either method is generally followed by subsequent heat treatment or annealing of the fiber.

The present compounds are sufficiently compatible with the resin that they become an integral part of the fiber, yet the incompatibility imparted by the fluorinated groups, and the mobility of the compounds, is sufficient to concentrate the compounds at the surface of the fiber, making the fiber hydrophobic and oleophobic. Once incorporated into the fiber surface, the present compounds resist being abraded or washed away because of the low solubility of the compounds in aqueous soap solutions and dry cleaning solvents. The present compounds also allow satisfactory dyeing of the treated fiber, or may be applied together with a dyestuff from the same batch.

The present invention also includes polyester and nylon fibers, especially those derived from polyethylene terephthalate (PET) and nylon-6 and nylon-66, which have incorporated therewith the compound or composition as defined above, and a process for producing such fibers which comprises contacting the fiber with a liquid emulsion, dispersion or solution containing the compound or composition as defined above, and thereafter heat treating or annealing the fiber to impart oil and water repellency.

DESCRIPTION OF THE PREFERRED EMBODIMENTS

Compounds falling within the above-identified general formula that are preferred are those wherein $R_f$ is $W(C_nF_{2n})Y$ wherein W is alkylene of 2 to 6 carbon atoms, n is 2 to 12 and Y is hydrogen, fluoro, or perfluoroalkoxy of 1 to 6 carbon atoms. Especially preferred are those compound wherein $R_f$ is selected from $-CH_2CH_2(CF_2)_gCF_3$ or $-CH_2CH_2(CF_2)_h OCF(CF_3)_2$ wherein g is 5 to 11 and h is 4 to 10. Most preferred are compounds of formula I wherein $R_f$ is $-CH_2CH_2(CF_2CF_2)_jCF_2CF_3$ and j is 2 to 5.

The compounds of the present invention may be readily prepared by reaction of 2,4-bis(p-isocyano benzyl)phenyl isocyanate

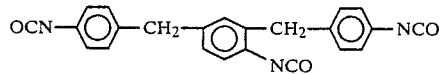

with the selected fluorinated alcohol ($R_f$-OH) to form the corresponding carbamate. The reaction of isocyanates with alcohols is well-known in the art and this reaction proceeds accordingly. Commercially available mixtures of polyisocyanates containing at least 10% of the above-described tri-isocyanate may be advantageously employed to produce the soil repellent carbamate compositions of the present invention upon reaction with an equivalent of fluorinated alcohol (i.e. sufficient alcohol to esterify all of the isocyanate groups).

The fluorinated radicals $R_f$ which may be present in the compounds of this invention are derived from the corresponding fluorinated alcohols ($R_f$-OH) which are known in the art and described in U.S. Pat. No. 3,171,861, U.S. Pat. No. 3,514,487, U.S. Pat. No. 3,646,153, U.S. Pat. No. 3,697,564, U.S. Pat. No. 4,209,610 and 4,219,681, all of which are incorporated herein by reference.

Typical of these are fluorinated alcohols of the formula $HO-W(C_nF_{2n})Y$ wherein W has from 1 to 10 carbon atoms and is selected from alkylene and $W'-Z-(W'')_b$ where W' and W'' are alkylene, Z is O, S, NHCO, or $N(R)SO_2$ wherein R is H or lower alkyl, and b is 0 or 1, Y is hydrogen, fluoro, or perfluoroalkoxy of 1 to 6 carbon atoms, and n is 2 to 20. The preferred fluorinated alcohols, because of their commercial availability, are the perfluoroalkylethanols and omega-perfluoroisopropoxy-perfluoroalkyl ethanols having two to twelve carbon atoms in the perfluoroalkyl groups, as well as the propanol homologues thereof. Most preferred are the perfluoroalkyl ethanols having six to twelve carbon atoms in the perfluoroalkyl groups, and mixture thereof.

The soil-repellent compounds of the present invention may be incorporated into polyester or nylon fibers using several known methods. In one method the compound is blended with the resin prior to being extruded into fibers. In another method, the compound may be applied to the fiber by absorption from a liquid medium, for example as a solution in an organic solvent or as an emulsion or dispersion in aqueous medium. In either method the fibers are generally annealed at elevated temperatures after treatment. Typically the compounds are incorporated in the fibers in an amount of from about 0.1 to 1% by weight and the treated fibers are annealed at temperatures of about 100° to 220° C. for about 1 to 240 minutes to impart the desired soil repellency. Further details of the above methods are disclosed in U.S. Pat. No. 4,209,610 and U.S. Pat. No. 4,219,625 which are incorporated herein by reference.

The invention may be described in greater detail by the following examples in which the parts and percentages are by weight. In each of the examples the fluorinated alcohol employed is a mixture of perfluoroalkyl ethanols having six to twelve carbon atoms in the perfluoroalkyl group. The composition prepared in each Example is a mixture of the compounds of formula I and formula II as previously depicted, the percentages of which are stated for each example (based on analysis of isocyanate by gas chromatography). Where the stated percentages do not total 100%, the remainder of the composition comprises primarily isomers and homologues of I and II, as well as a small amount of other impurities carried over from the starting materials.

EXAMPLE 1

In a 500 ml 4-necked flask was added 6.58 g (0.02 mole) 2,4-bis(p-amino benzyl) aniline (DuPont BABA) and 150 ml toluene. The mixture was heated to 90° C. to effect solution and HCl gas added subsurface until excess had been added. The slurry was well agitated. Eighty-eight ml of 12.5% phosgene in toluene was added subsurface over one hour keeping the temperature above 130° C. The mixture was stirred one hour longer and then purged with nitrogen to remove excess phosgene. The mixture was filtered to remove unwanted solids, an equivalent amount of perfluoroalkylethanol was added, and the mixture refluxed until the G.C. analysis showed no further reaction of the alcohol. the solvent was removed by steam distillation to yield 18.6 g of an off-white solid. Assay: I—90%; II—6%.

EXAMPLE 2

In a 100 ml 3-necked flask was added 22.9 g perfluoroalkylethanol (0.05 equiv.) and 6.75 g (0.05 equiv.) polyisocyanate Lupranate M-20 (BASF). The mixture was heated to 85° C. and after three hours 20 ml of N-methylpyrrolidone was added to the thick solution. The mixture was heated another three hours at 85° C. until no further reaction took place as evidenced by the G.C. analysis for alcohol. The mixture was poured into 400 ml ice water, washed and filtered to give 28 g of light tan solid. Assay: I—34%; II—60%.

EXAMPLE 3

In a 100 ml 3-necked flask was added 6.75 g (0.05 equiv.) polyisocyanate Mondur MRS (Mobay) and 22.9 g perfluoroalkylethanol (0.05 equiv.). The mixture was heated at 85° C. for 1.5 hours. Ten ml of N-methylpyrrolidone was added and the mixture heated ten hours longer. The reaction was worked up as in Example II to yield a light tan solid. Assay: I—19%, II—50%.

EXAMPLE 4

Chlorobenzene (400 ml) was added to polyisocyanate Hylene M-50 (250 g; 0.5 mole) and heated to 40° C. while stirring. Then 450 g (1 mole) perfluoroalkylethanol was added and the mixture heated to 85° C. and held for four hours. The chlorobenzene was removed by steam distillation and the residual material filtered and dried under vacuum to yield 513 g of yellowish solid. Assay: I—23%; II—72%.

EXAMPLE 5

Equal parts of the composition of Example 4 and the dicarbamate of Comparative Example B were thoroughly blended to yield a composition having Assay: I—11%; II—86%.

EXAMPLE 6

A blend of 11 g of the composition of Example 1 and 89 g of the dicarbamate of comparative Example B was prepared, yielding a composition of Assay: I—10%; II—90%.

COMPARATIVE EXAMPLES

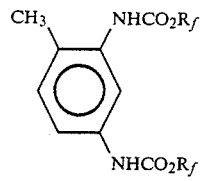

A.

In a 100 ml flask was added 4.49 g of 97% toluene di-isocyanate(0.025 mole), 22.9 g (0.05 mole) perfluoroalkylethanol and 10 ml N-methylpyrrolidone. The mixture was heated at 70° C. for eight hours and drowned into ice water. After washing to remove solvent, the material was filtered and dried under vacuum, yielding 23 g of off-white powder.

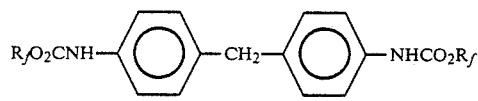

B.

In a 100 ml 3-necked flask was added 22.9 g perfluoroalklethanol (0.05 mole) which was heated to 85° C. To this was added 6.25 g (0.025 moles) 4,4'-methylene di-phenyl isocyanate Mondur M, Mobay). The reaction temperature was increased to 130° C. and held for one hour. On cooling 27 g of a white solid was obtained.

Application of Compounds to Fiber

Each of the compounds prepared in Examples 1 to 5 and Comparative Examples A and B were applied to fiber by dissolving the compound in acetone and applying it to nylon fabric through a padder. The concentration of compound in solution was adjusted so that pick up was 0.25% compound compared to the weight of the fabric. After drying at room temperature, the fabric was cured (annealed) at 140° C. for 30 minutes.

The treated fabrics were then subjected to AATCC Test 61-1968 Wash IIA or IIIA using a launderometer from Atlas Electric Company to simulate five home launderings at medium or high temperature settings. The washed fabric was evaluated for oil repellency according to AATCC Test 118-1975, the rating scale running from 0–8 with increasing numbers indicating greater repellency. Each fabric was also tested before washing as well as after the wash tests. For long term washfastness the more rigorous IIIA Test was carried out repeatedly, each repeat simulating five home launderings at high temperature. The results of the testing for oil repellency are shown in Table I.

TABLE I

| Example | Composition | Before Washing | After IIA Wash | After IIIA Wash 1× | 2× | 3× | 4× | 5× |
|---|---|---|---|---|---|---|---|---|
| 1 | I - 90% II - 6% | 6 | 6 | 6 | 6 | 6 | 6 | 6 |
| 2 | I - 34% II - 60% | 6 | 6 | 6 | 6 | 6 | 6 | 6 |
| 3 | I - 19% II - 50% | 6 | 6 | 6 | 6 | 6 | 6 | 6 |
| 4 | I - 23% II - 72% | 6 | 6 | 6 | 6 | 6 | 6 | 6 |
| 5 | I - 11% II - 86% | 6 | — | 6 | 5 | 4 | 3 | 2 |
| 6 | I - 10% II - 90% | 6 | 3 | 1 | 0 | — | — | — |
| A | toluene dicarbamate | 0* | 0 | — | — | — | — | — |
| B | II - 100% | 6 | 0** | 0 | 0 | — | — | — |

*Oil repellency measured 5 after padding and drying, 0 after annealing.
**In one test a 3 was obtained, but this result could not be repeated.

What is claimed is:

1. A compound of the formula

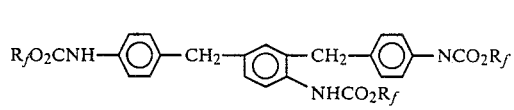 (I)

wherein $R_f$ is a fluorinated radical of the formula $-W(C_nF_{2n})Y$ wherein W has from 1 to 10 carbon atoms and is selected from alkylene and $W'-Z-(W'')_b$ where W' and W'' are alkylene, Z is O, S, NHCO, or $N(R)SO_2$ wherein R is H or lower alkyl, and b is 0 or 1, Y is hydrogen, fluoro, or perfluoroalkoxy of 1 to 6 carbon atoms, and n is 2 to 20.

2. A compound according to claim 1 wherein W is alkylene of 2 to 6 carbon atoms and n is 2 to 12.

3. A compound according to claim 1 wherein $R_f$ is selected from $-CH_2CH_2(CF_2)_gCF_3$ or $-CH_2CH_2(CF_2)_hOCF(CF_3)_2$ wherein g is 5 to 11 and h is 4 to 10.

4. A compound according to claim 1 wherein $R_f$ is $-CH_2CH_2(CF_2CF_2)_jCF_2CF_3$ and j is 2 to 5.

5. A composition comprising at least 10% of a compound of the formula (I)

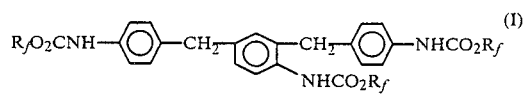 (I)

in admixture with from 90 to 5% of a compound of the formula (II)

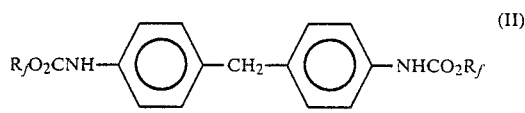 (II)

wherein $R_f$ is a fluorinated radical of the formula $-W(C_nF_{2n})Y$ wherein W has from 1 to 10 carbon atoms and is selected from alkylene and $W'-Z-(W'')_b$ were W' and W'' are alkylene, Z is O, S, NHCO, or $N(R)SO_2$ wherein R is H or lower alkyl, and b is 0 or 1, Y is hydrogen, fluoro, or perfluoroalkoxy of 1 to 6 carbon atoms, and n is 2 to 20.

6. A composition according to claim 5 wherein W is alkylene of 2 to 6 carbon atoms and n is 2 to 12.

7. A composition according to claim 5 wherein $R_f$ is selected from $-CH_2CH_2(CF_2)_gCF_3$ or $-CH_2CH_2(CF_2)_hOCF(CF_3)_2$ wherein g is 5 to 11 and h is 4 to 10.

8. A composition according to claim 5 wherein $R_f$ is $-CH_2CH_2(CF_2CF_2)_jCF_2CF_3$ and j is 2 to 5.

9. A composition according to claim 5 which additionally comprises 0 to 30% of isomers and homologues of compounds I and II.

10. A composition according to claim 5 comprising from 15 to 40% of Compound (I) and from 50 to 80% of Compound (II).

* * * * *